United States Patent
Nishimura et al.

(10) Patent No.: US 11,364,206 B2
(45) Date of Patent: Jun. 21, 2022

(54) SEAMLESS CAPSULE SHELL COMPOSITION AND SEAMLESS CAPSULE

(71) Applicants: Fuji Capsule Co., Ltd., Shizuoka (JP); Nisshin Kasei Co., Ltd., Osaka (JP)

(72) Inventors: Koichi Nishimura, Shizuoka (JP); Sergio Ishiba, Shizuoka (JP); Hitoshi Uruga, Shizuoka (JP); Hisayoshi Aoki, Shizuoka (JP); Yosuke Kondo, Shizuoka (JP); Yoshiyuki Shimokawa, Shizuoka (JP)

(73) Assignees: FUJI CAPSULE CO., LTD., Shizuoka (JP); NISSHIN KASEI CO., LTD., Osaka (JP)

( * ) Notice: Subject to any disclaimer, the term of this patent is extended or adjusted under 35 U.S.C. 154(b) by 196 days.

(21) Appl. No.: 16/619,272

(22) PCT Filed: Jun. 6, 2018

(86) PCT No.: PCT/JP2018/021666
§ 371 (c)(1),
(2) Date: Dec. 4, 2019

(87) PCT Pub. No.: WO2018/225770
PCT Pub. Date: Dec. 13, 2018

(65) Prior Publication Data
US 2020/0155464 A1  May 21, 2020

(30) Foreign Application Priority Data

Jun. 9, 2017  (JP) .............................. JP2017-114203

(51) Int. Cl.
*A61K 9/48* (2006.01)
*A61K 47/38* (2006.01)
*A61K 47/10* (2017.01)
*A61K 47/26* (2006.01)
*A61K 47/32* (2006.01)

(52) U.S. Cl.
CPC ............ *A61K 9/4816* (2013.01); *A61K 47/38* (2013.01); *A23V 2002/00* (2013.01); *A61K 47/10* (2013.01); *A61K 47/26* (2013.01); *A61K 47/32* (2013.01)

(58) Field of Classification Search
None
See application file for complete search history.

(56) References Cited

U.S. PATENT DOCUMENTS

| | | | | |
|---|---|---|---|---|
| 2012/0316250 A1* | 12/2012 | Moriuchi | ................ | A61J 3/077 514/772.4 |
| 2014/0234411 A1* | 8/2014 | Kamaguchi | ............. | A23P 10/30 424/455 |

FOREIGN PATENT DOCUMENTS

| | | |
|---|---|---|
| EP | 1323404 A1 | 7/2003 |
| JP | 63-238015 A | 10/1988 |
| JP | 9-25228 A | 1/1997 |
| JP | 10-291928 A | 11/1998 |
| JP | 2007-91670 A | 4/2007 |
| JP | 2017-105732 A | 6/2017 |
| WO | 2002/017848 A1 | 3/2002 |
| WO | 2005/019286 A1 | 3/2005 |
| WO | 2006/121098 A1 | 11/2006 |
| WO | 2006/106799 A1 | 12/2006 |
| WO | 2017/022248 A1 | 2/2017 |

* cited by examiner

*Primary Examiner* — Nannette Holloman
(74) *Attorney, Agent, or Firm* — Edwin S. Flores; Daniel J. Chalker; Chalker Flores, LLP

(57) ABSTRACT

The present invention addresses a problem of providing a high quality seamless capsule, with excellent uniformity of shell thickness and virtually no eyes in the shell.

The problem can be solved by manufacturing a seamless capsule using a shell composition comprising at least one polysaccharide selected from the group consisting of agar, carrageenan and gellan gum, and a PVA copolymer comprising the following structural units: (i) polyvinyl alcohol, (ii) at least one unsaturated carboxylic acid selected from the group consisting of acrylic acid, methacrylic acid, fumaric acid and maleic acid, and (iii) at least one unsaturated carboxylic acid ester selected from the group consisting of compounds represented by formula [I]:

$$H_2C=C(R^1)-COOR^2 \qquad [I]$$

(wherein $R^1$ represents a hydrogen atom or a methyl group, and $R^2$ represents an alkyl group having 1 to 4 carbon atoms).

7 Claims, No Drawings

SEAMLESS CAPSULE SHELL COMPOSITION AND SEAMLESS CAPSULE

CROSS-REFERENCE TO RELATED APPLICATIONS

This application is the National Stage of International Application No. PCT/JP2018/021666, filed on Jun. 6, 2018 claiming the priority of JP 2017-114203, filed on Jun. 9, 2017, the content of each of which is incorporated by reference herein.

TECHNICAL FIELD OF THE INVENTION

The present invention relates to a shell composition (hereinafter referred to as "the present shell composition" in some cases) in a seamless capsule, including at least one polysaccharide selected from the group consisting of agar, carrageenan and gellan gum (hereinafter referred to as "agar and the like" in some cases) and a specific polyvinyl alcohol copolymer (PVA copolymer).

BACKGROUND OF THE INVENTION

Capsules are widely used in the field of pharmaceuticals, foods, quasi-drugs and the like. The capsules include hard capsules and soft capsules. A seamless capsule is one type of soft capsules, which is manufactured by utilizing a tension occurring in the oil-water interface and gelling properties of a shell base material. The seamless capsule has various advantages such as a wide selection range of the particle size, a wide selection range of the film thickness or the film hardness of the shell of a capsule, and a wide selection range of the dissolution time of a capsule.

In manufacture of a seamless capsule, an interface tension adjusting agent and a gelling accelerator (for example, fat, phospholipids and a polar organic solvent such as ethanol) are mixed in a shell composition or a capsule fill in order to obtain a high quality capsule by suppressing the occurrence of eyes (droplets of the content occurring in a shell) or thickness deviation (significant difference in film thickness of a shell). Further, as a shell forming material to form a seamless capsule (a shell composition), gelatin is used, which has excellent solubility in the body, so that the rapid disintegration allows a content to be released. However, a problem was that, since gelatin has an amino group, in a case where an aldehyde group-containing material such as reducing sugar and macrolide antibiotics or a material which produces an aldehyde through reaction over time is present in a capsule fill, the amino group of gelatin is chemically bonded to the aldehyde group in the content during storage to cause discoloration or insolubilization of the shell, resulting in a problem of delayed release of the content.

Meanwhile, a PVA copolymer is a copolymer having polyvinyl alcohol (PVA) as a structural unit. For example, use of a PVA copolymer as a film coating agent of tablets or granules has been reported (Patent Document 1). Also, a hard capsule made from a PVA copolymer as raw material has been reported (Patent Document 2). Further, a colored capsule including a PVA copolymer, a gelling agent such as carrageenan, and a chromatic coloring has been reported (Patent Document 3). However, a seamless capsule made from a PVA copolymer and agar and the like as shell material has not been specifically manufactured so far, and the effect thereof has not been known.

PRIOR ART DOCUMENTS

Patent Documents

Patent Document 1: International Publication No. WO 2005/019286
Patent Document 2: International Publication No. WO 2002/017848
Patent Document 3: Japanese unexamined Patent Application Publication No. 2007-91670

SUMMARY OF THE INVENTION

Object to be Solved by the Invention

An object of the present invention is to provide a high quality seamless capsule excellent in uniformity of the shell thickness, with virtually no eyes in the shell.

Means to Solve the Object

The present inventors have continued intensive studies to solve the problem described above. In the process, it has been found that use of a shell composition comprising agar and the like and a specific PVA copolymer (the present shell composition) enables a high quality seamless capsule excellent in uniformity of the shell thickness, with virtually no eyes in the shell, to be manufactured, so that the present invention has been completed.

In other words, the present invention is as follows.

[1] A shell composition of seamless capsules comprising: at least one polysaccharide selected from the group consisting of agar, carrageenan and gellan gum; and a polyvinyl alcohol copolymer, wherein
the polyvinyl alcohol copolymer comprises the following as structural units:
(i) polyvinyl alcohol,
(ii) at least one unsaturated carboxylic acid selected from the group consisting of acrylic acid, methacrylic acid, fumaric acid and maleic acid, and
(iii) at least one unsaturated carboxylic acid ester selected from the group consisting of compounds represented by formula [I]:

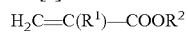

$$H_2C=C(R^1)-COOR^2 \qquad [I]$$

(wherein $R^1$ represents a hydrogen atom or a methyl group, and $R^2$ represents an alkyl group having 1 to 4 carbon atoms).

[2] The shell composition according to item [1] described above, wherein the unsaturated carboxylic acid is acrylic acid.

[3] The shell composition according to item [1] or [2] described above, wherein the unsaturated carboxylic acid ester is methyl methacrylate.

[4] The shell composition according to any one of items [1] to [3] described above, further comprising one or more plasticizers.

[5] The shell composition according to item [4] described above, wherein the one or more plasticizers comprise glycerol and sorbitol.

[6] A seamless capsule obtainable by using the shell composition according to any one of items [1] to [5] described above.

DETAILED DESCRIPTION OF THE INVENTION

The seamless capsule manufactured using the present shell composition has high quality, with excellent uniformity of the shell thickness of the capsule and virtually no eyes in the shell, being useful in the fields of foods, pharmaceuticals, cosmetics and the like.

Mode of Carrying Out the Invention

The present shell composition is a composition for use in a shell (capsule shell) covering the capsule fill in a seamless capsule (referred to as a core material or filling material), comprising agar and the like and a PVA copolymer (hereinafter, referred to as "the present PVA copolymer" in some cases) comprising (i) polyvinyl alcohol, (ii) at least one unsaturated carboxylic acid selected from the group consisting of acrylic acid, methacrylic acid, fumaric acid and maleic acid, and (iii) at least one unsaturated carboxylic acid ester selected from the group consisting of compounds represented by formula [I]:

$$H_2C=C(R^1)-COOR^2 \qquad [I]$$

(wherein $R^1$ represents a hydrogen atom or a methyl group, and $R^2$ represents an alkyl group having 1 to 4 carbon atoms), as structural units. The "structural units" mean monomers in the (co-)polymer prior to polymerization.

The present shell composition is roughly classified into a liquid type and a non-liquid type. The present shell composition of a liquid type is usually made of solvent (e.g. purified water) including agar and the like and the present PVA copolymer. The present shell composition of a non-liquid type is usually made of material containing powder agar and the like and the present PVA copolymer. The present shell composition of a non-liquid type is added to a solvent (e.g., purified water), mixed, stirred, and heated (usually in a range of 85 to 100° C., preferably 85 to 93° C.) to be melted, so that the present shell composition of a liquid type can be prepared.

The agar described above is a polysaccharide obtained from red algae such as agar weed (Tengusa) and false ceylon mosses, having a basic skeleton of galactose. As the agar described above, ones prepared from red algae by a method described in, for example, Japanese unexamined Patent Application Publication No. 2009-225671, Japanese unexamined Patent Application Publication No. 2001-78726 and Japanese unexamined Patent Application Publication No. 5-184331 may be used, or a commercially available product may be used. Examples of the agar commercially available include agar PS-26 according to Japanese Pharmacopoeia, agar PS-10 according to Japanese Pharmacopoeia, Ina agar PC-6F, Ultra Agar AX-30 (all of the above manufactured by Ina Food Industry Co., Ltd.), and powdered agar JS-1000 (manufactured by Asahi Co., Ltd.).

The carrageenan described above is one of straight-chain sulfur-containing polysaccharides extracted from red algae by alkali, being an anionic polymer compound made of D-galactose (or 3,6-anhydro-D-galactose) and sulfuric acid. The carrageenan has a composition similar to agarose (main component of agar) obtained from red algae in the same manner, but differs in that it includes a large amount of sulfuric acid. The carrageenan is classified into three types including κ-type τ-type and λ-type depending on the properties, and in the present invention, κ-type which forms a more rigid gel is preferred.

The gellan gum described above is a water-soluble polysaccharide synthesized by *Sphingomonas erodia* which is microorganism parasitic on aquatic plants, the polysaccharide being classified into a complex polysaccharide (heteropolysaccharide), which is a polymer having repeating units of tetrasaccharide consisting of two D-glucose residues, one L-rhamnose residue and one D-glucuronic acid residue. The gellan gum has two types including a native type having two hydroxyl groups substituted with an acetyl group and a glyceryl group, and a deacylation type with removal of such substitution. In the present invention, the deacylation type is preferred.

Agar and the like described above are polysaccharides derived from aquatic organisms or microorganisms parasitic on aquatic organisms, having common properties as polysaccharides exhibiting acidity in an aqueous solution due to having a carboxylic acid residue in the molecule.

The jelly strength of the agar and the like described above may be in a range where formability of a seamless capsule is not impaired, for example, 100 g/cm² or more, preferably 200 g/cm² or more, more preferably 400 g/cm² or more, still more preferably 500 g/cm² or more, furthermore preferably 600 g/cm² or more. With an excessively high jelly strength of agar and the like, it may become difficult to crush seamless capsule with fingers. The jelly strength of the agar and the like described above, therefore, is preferably 2000 g/cm² or less, more preferably 1800 g/cm² or less, still more preferably 1600 g/cm² or less, furthermore preferably 1400 g/cm² or less, particularly preferably 1200 g/cm² or less.

In the present specification, "jelly strength of agar and the like" means the maximum withstand load (g) per 1 cm² of the surface area of the gel for 20 seconds, the gel such as agar and the like being prepared by leaving an aqueous solution of 1.5 mass % agar and the like to stand at 20° C. for 15 hours for solidification. The hardness of the gel of agar and the like can be measured using a Nikkansui-type jelly strength measuring apparatus (manufactured by Kiya Seisakusho, Co., Ltd.).

The concentration of agar and the like in the present shell composition is not particularly limited, and in the case of the present shell composition of a liquid type, for example, in a range of 1.0 to 30 mass %, preferably 1.0 to 10 mass %, more preferably 1.0 to 6.0 mass %, still more preferably 1.0 to 3.0 mass %. Also, in the case of the present shell composition of a non-liquid type, the concentration is, for example, in a range of 1.0 to 60 mass %, preferably 1.0 to 40 mass %, more preferably 2.0 to 20 mass %, still more preferably 5.0 to 9.0 mass %.

Polyvinyl alcohol is usually produced by radical-polymerizing vinyl acetate in methanol solvent, and substituting some of or the whole of acetic acid groups of the resulting polyvinyl acetate with hydroxy groups (saponification) using sodium hydroxide in the methanol solution. The polyvinyl alcohol is therefore usually classified into a completely saponified product, an intermediately saponified product and a partially saponified product, depending on the saponification degree, i.e., the difference in the ratio (mol %) of hydroxyl group relative to the total number of acetic acid groups and hydroxyl groups in the polyvinyl alcohol.

The saponification degree of (i) polyvinyl alcohol described above is not particularly limited, for example, in the range of 70 to 99 mol %, preferably 75 to 96 mol %, more preferably 80 to 94 mol %, still more preferably 85 to 90 mol %. Also, the average polymerization degree of (i) polyvinyl alcohol described above is, but not particularly limited to, for example, 100 to 4000, preferably 300 to 3000, more preferably 400 to 2000, still more preferably 500 to 1800. Also, (i) polyvinyl alcohol described above may be used alone or in combination of two or more thereof having difference in the saponification degree and the average polymerization degree.

As (i) polyvinyl alcohol described above, polyvinyl alcohol having a desired saponification degree and a desired average polymerization degree may be specially prepared, or a commercially available product may be used. Examples of polyvinyl alcohol commercially available include Gohsenol (registered trademark) EGOS (manufactured by Nippon Synthetic Chemical Industry Co., Ltd.), EG25 and EG40 (all of which manufactured by Nippon Synthetic Chemical Industry Co., Ltd.), PVA203, PVA204 and PVA205 (all of which manufactured by Kuraray Co., Ltd.), and JP-04 and JP-05 (all of which manufactured by Japan VAM & Poval Co., Ltd.).

Specific examples of (ii) unsaturated carboxylic acid described above include one of acrylic acid, methacrylic acid, fumaric acid and maleic acid; a combination of two such as acrylic acid and methacrylic acid, acrylic acid and fumaric acid, acrylic acid and maleic acid, methacrylic acid and fumaric acid, methacrylic acid and maleic acid, or fumaric acid and maleic acid; a combination of three such as acrylic acid, methacrylic acid and fumaric acid, acrylic acid, methacrylic acid and maleic acid, or methacrylic acid, fumaric acid and maleic acid; and a combination of four such as acrylic acid, methacrylic acid, fumaric acid and maleic acid. One and combinations of two to four comprising acrylic acid are preferred, and acrylic acid alone is more preferred.

Specific examples of (iii) unsaturated carboxylic acid ester include at least one selected from the group consisting of methyl methacrylate, methyl acrylate, ethyl methacrylate, ethyl acrylate, propyl methacrylate, propyl acrylate, isopropyl methacrylate, isopropyl acrylate, butyl methacrylate, butyl acrylate, isobutyl methacrylate, and isobutyl acrylate; preferably at least one selected from the group consisting of methyl methacrylate, methyl acrylate, ethyl methacrylate and ethyl acrylate; more preferably at least one selected from the group consisting of methyl methacrylate and methyl acrylate; still more preferably methyl methacrylate.

The mass ratio between (ii) unsaturated carboxylic acid and (iii) unsaturated carboxylic acid ester comprised in the present PVA copolymer is, but not particularly limited to, for example, 20 to 98 mass % of (iii) unsaturated carboxylic acid ester relative to 2 to 80 mass % of (ii) unsaturated carboxylic acid, preferably 50 to 95 mass % of (iii) unsaturated carboxylic acid ester relative to 5 to 50 mass % of (ii) unsaturated carboxylic acid, more preferably 60 to 90 mass % of (iii) unsaturated carboxylic acid ester relative to 10 to 40 mass % of (ii) unsaturated carboxylic acid, still more preferably 70 to 90 mass % of (iii) unsaturated carboxylic acid ester relative to 10 to 30 mass % of (ii) unsaturated carboxylic acid, furthermore preferably 80 to 90 mass % of (iii) unsaturated carboxylic acid ester relative to 10 to 20 mass % of (ii) unsaturated carboxylic acid. In other words, the mass ratio of (ii) unsaturated carboxylic acid relative to the total amount of (ii) unsaturated carboxylic acid and (iii) unsaturated carboxylic acid ester (these are collectively referred to as "polymerizable vinyl monomers" in some cases) is, for example, 2 to 80 mass %, preferably 5 to 50 mass %, more preferably 10 to 40 mass %, still more preferably 10 to 30 mass %, furthermore preferably 10 to 20 mass %. Also, the mass ratio of (iii) unsaturated carboxylic acid ester relative to the total amount of the polymerizable vinyl monomers is, for example, 20 to 98 mass %, preferably 50 to 95 mass %, more preferably 60 to 90 mass %, still more preferably 70 to 90 mass %, furthermore preferably 80 to 90 mass %.

In a case where acrylic acid alone is used as (ii) unsaturated carboxylic acid described above and methyl methacrylate alone is used as (iii) unsaturated carboxylic acid ester described above, the mass ratio of (i) polyvinyl alcohol:(ii) acrylic acid:(iii) methyl methacrylate is preferably 60 to 90 mass %:0.5 to 12 mass %:7 to 38 mass %, more preferably 70 to 90 mass %:1 to 5 mass %:10 to 25 mass %.

The concentration of the present PVA copolymer in the present shell composition is, but not particularly limited to, for example, in a range of 10 to 70 mass %, preferably 10 to 60 mass %, more preferably 10 to 50 mass %, still more preferably 20 to 40 mass %, in the case of the present shell composition of a liquid type. Also, in the case of the shell composition of a non-liquid type, the concentration is, for example, in a range of 40 to 97 mass %, preferably 50 to 96 mass %, more preferably 60 to 93 mass %, still more preferably 70 to 90 mass %.

The present PVA copolymers may be produced using a known method. For example, the production may be performed by adding (i) polyvinyl alcohol into water such as deionized water, raising the temperature (e.g., 90 to 100° C.) to dissolve polyvinyl alcohol, then adding (ii) unsaturated carboxylic acid and (iii) unsaturated carboxylic acid ester thereto, performing nitrogen purge, and adding polymerization initiator for copolymerization. Depending on the mass ratio of (i) polyvinyl alcohol to (ii) unsaturated carboxylic acid to (iii) unsaturated carboxylic acid ester added to water, the mass ratio of (i) polyvinyl alcohol to (ii) unsaturated carboxylic acid to (iii) unsaturated carboxylic acid ester in the present PVA copolymer is determined. The mass ratio of each component added to water is preferably the same as the mass ratio of each component in the present PVA copolymer.

Examples of the polymerization initiator include an azo compound such as 2,2'-azobis(2-amidinopropane)hydrochloride and AIBN (azoisobutyronitrile); a persulfate such as potassium persulfate, sodium persulfate and ammonium persulfate; an organic peroxide such as t-butyl hydroperoxide; and a redox initiator such as hydrogen peroxide-tartaric acid and hydrogen peroxide-sodium tartrate.

The present PVA copolymer has a structure in which at least one of (ii) unsaturated carboxylic acid or (iii) unsaturated carboxylic acid ester as polymerizable vinyl monomers is graft polymerized with —OCOCH$_3$ group present as a side chain of polyvinyl alcohol. In the graft polymerization, polyvinyl alcohols may be bonded to each other through "a polymer with at least one of polymerizable vinyl monomers polymerized or copolymerized". In other words, a polyvinyl alcohol and another polyvinyl alcohol may be cross-linked by "a polymer with at least one of polymerizable vinyl monomers polymerized or copolymerized".

For example, in a case where (ii) acrylic acid and (iii) methyl methacrylate are used, the present PVA copolymer has a structure in which a copolymer of acrylic acid and methyl methacrylate is bonded to polyvinyl alcohol through the —OCOCH$_3$ group of polyvinyl alcohol.

Specific examples of the PVA copolymer (poly vinyl alcohol-acrylic acid-methyl methacrylate copolymer) include a PVA copolymer described in Japanese unexamined Patent application Publication No. 2016-008294.

The present shell composition preferably further comprises one or more plasticizers to impart flexibility to the shell after forming. Examples of the plasticizer include a polyhydric alcohol such as glycerol, polyethylene glycol, propylene glycol and polypropylene glycol; a monosaccharide such as dextrose, fructose, glucose and galactose; a disaccharide such as sucrose, maltose, trehalose and coupling sugar; an oligosaccharide such as maltooligosaccharide; a sugar alcohol such as sorbitol, maltitol, lactitol, palatinit, xylitol, mannitol and galactitol; polyvinyl alcohol; triacetin; a starch derivative such as polydextrose, dextrin, maltodextrins, indigestible dextrin, cyclodextrin ($\alpha$, $\beta$, or $\gamma$);

starch; and a cellulose derivative such as hydroxymethyl cellulose (HPMC), hydroxypropyl cellulose (HPLC), methylcellulose (MC) and carboxymethyl cellulose (CMC). Plasticizers including glycerol and sorbitol are preferred.

The concentration of the plasticizer in the present shell composition is not particularly limited, and in the case of the present shell composition of a liquid type, the concentration is, for example, in a range of 1.0 to 30 mass %, preferably 1.0 to 20 mass %, more preferably 1.0 to 10 mass %, still more preferably 2.0 to 5.0 mass %. Also, in the case of the present shell composition of a non-liquid type, the concentration is, for example, in a range of 1.0 to 60 mass %, preferably 1.0 to 40 mass %, more preferably 2.0 to 20 mass %, still more preferably 5.0 to 9.0 mass %.

Although the present shell composition may comprise one or more gelling agents other than agar and the like selected from the group consisting of locust bean gum, gum arabic, pectin, guar gum, alginic acid, pullulan, konjac gum, gelatin, tara gum and glucomannan, ones hardly containing these gelling agents (usually 0.1 mass % or less, preferably 0.01 mass % or less, more preferably 0.001 mass % or less) or ones not containing these at all are preferred.

Examples of optional components in the present shell composition include a colorant such as pigment, food coloring, and dye; a light-shielding agent such as magnesium oxide and titanium dioxide; a surfactant such as sodium lauryl sulfate and fatty acid ester; a flavoring agent; a flavoring substance; a preservative; and a fragrance. In the present specification, "optional component" means a component that may or may not be included.

In the present invention, the capsule fill that can be contained in the seamless capsule is not particularly limited as long as it can be encapsulated in the seamless capsule and does not invade the capsule shell, and examples thereof include oils, waxes, fatty acids, vitamins, pharmaceuticals, foods, wetting agents, moisturizing agents, antioxidants, preservatives, astringents, whitening agents, organic acids and fragrances. In particular, since the seamless capsule can prevent insolubilization of the capsule caused by a substance containing an aldehyde group and reduce the oxidation of the capsule fills, the seamless capsule can contain a substance containing an aldehyde group as capsule fill. From the viewpoint of taking advantage of characteristics of the seamless capsule, for example, a filling liquid of a component containing an aldehyde group or a component easily oxidized dissolved in a fatty acid triglyceride or polyethylene glycol solution is particularly preferred. Examples of the component containing an aldehyde group include various reducing sugars (e.g., glucose, fructose, lactose, arabinose and maltose), citral, vanillin, benzaldehyde, glutaraldehyde, o-bromobenzaldehyde, butanal, chlorobutanal, furfural, hydroxymethylfurfural, perillaldehyde, acrolein, and aldosterone. The capsule fill described above is usually a liquid type.

In the present invention, the seamless capsule may be manufactured (prepared) from the present shell composition and a capsule fill using a capsule manufacturing apparatus usually used in production of seamless capsules such as SPHEREX (manufactured by Freund Sangyo Co., Ltd.) or a seamless capsule manufacturing apparatus (manufactured by Fuji Capsule Co., Ltd.) by a submerged dropping method using a multiple nozzle for both components (the present shell composition and the capsule fill). For example, using a concentric double nozzle, the present shell composition of a liquid type as it is or prepared is discharged from the outer nozzle, and the capsule fill is discharged from the inner nozzle, into a carrier liquid at constant rates, respectively.

The two-layer flowing liquid is cut at regular intervals to form droplets with interfacial tension, and then the outer shell layer (the present shell composition) is gelled by cooling, so that a seamless capsule with no joint can be manufactured. The submerged dropping method described above is also referred to as a submerged curing method or an orifice method. In some cases, a triple or more multiple nozzle is used. Since the mass content ratios of various components such as agar and PVA copolymer in the seamless capsule shell after manufacture are the same as the mass content ratios of those components included in the present shell composition of a liquid type as it is or prepared prior to the manufacture, the mass content ratios of various components in the seamless capsule shell after manufacture can be adjusted by adjusting the content of various components contained in the present shell composition of a liquid type as it is or prepared prior to the manufacture.

Also, the particle size of a capsule can be controlled by appropriately adjusting the discharge rate of the fill, the shell composition and the carrier liquid. Specifically, the fill is discharged at a discharge rate of 0.1 to 5 mL/min, the shell composition is discharged at a discharge rate of 0.1 to 10 mL/min, and the carrier liquid is discharged at a discharge rate of 15000 to 30000 mL/min, so that a soft capsule assembly having an average particle size of 900 μm or less, for example, 500 to 800 μm can be manufactured.

The size of a seamless capsule (particle size) manufactured using the present shell composition can be appropriately adjusted by a known method, preferably in a diameter range of 200 μm to 10 mm, more preferably in a diameter range of 400 μm to 6 mm, still more preferably in a diameter range of 600 μm to 4 mm.

The present invention is more specifically described with reference to Examples as follows, though the technical scope of the present invention is not limited thereto.

EXAMPLES

Examples 1 to 4

1. Manufacture of Seamless Capsule

The raw materials each shown in Table 1 (numbers in the table represent parts by mass unless otherwise specified) are mixed and stirred, then heated and dissolved while stirring (Example 1 at 95° C., Example 2 at 93° C., Example 3 at 80° C., and Example 4 at 80° C.) to prepare four types of shell compositions. The viscosity of Example 3 prepared was 64 mPa·s under condition at 80° C. immediately after preparation. Also, the viscosity of Example 1 prepared was 22 mPa·s under condition at 78° C. immediately after preparation, and the viscosity of Example 2 prepared was 41 mPa·s under condition at 82° C. immediately after preparation.

From the inner cylinder of a concentric double nozzle of a seamless capsule manufacturing apparatus (SPHEREX [formed tube diameter: 22 mm, vibration frequency: 25 Hz, tank temperature: 80° C., set temperature of cooling oil: 0° C.] manufactured by Freund Sangyo Co., Ltd.), a fill of 100 parts by mass of Millitol 318 (caprylic/capric triglyceride, manufactured by BASF) and 5 parts by mass of ethanol as core material was allowed to flow down, and from the outer cylinder, each of the four kinds of shell compositions as coating substances was allowed to flow down, respectively, so that a seamless capsule having a particle size (diameter) of 3 mm or 4 mm and a shell ratio of 20% was manufactured.

TABLE 1

| Raw material | Example 1 | Example 2 | Example 3 | Example 4 |
|---|---|---|---|---|
| PVA copolymer *[1] | 30 | 30 | 30 | 30 |
| Agar B*[2] | 2.5 | | | |
| Agar C*[3] | | 2.5 | | |
| κ-Carrageenan A*[4] | | | 2.5 | |
| Deacylated gellan gum *[5] | | | | 2.5 |
| Concentrated glycerol-S | 1.0 | 1.0 | 1.0 | 2.5 |
| D-sorbitol liquid | 2.5 | 2.5 | 2.5 | 1.0 |
| Purified water | 64 | 64 | 64 | 64 |

*[1] PVA copolymer described in Japanese unexamined Patent application Publication No. 2016-008294.
*[2] Refer to Table 2.
*[3] Refer to Table 3.
*[4] Refer to Table 4.
*[5] KELCOGEL (registered trademark) (manufactured by DSP Gokyo Food & Chemical Co., Ltd.)

TABLE 2

Specification of agar B

| Specification item | Standard value | Test method |
|---|---|---|
| Jelly strength | 1000 ± 50 g/cm$^2$ | Nikkansui-type (1.5%, 20° C. gel) |
| pH | 7.0 ± 1.0 | 1.5% Sol, pH meter |

TABLE 3

Specification of agar C

| Specification item | Standard value | Test method |
|---|---|---|
| Jelly strength | 650 ± 20 g/cm$^2$ | Nikkansui-type (1.5%, 20° C. gel) |
| pH | 5.5 ± 1.0 | 1.5% Sol, pH meter |

TABLE 4

Specification of κ-Carrageenan A

| Specification item | Standard value | Test method |
|---|---|---|
| pH | 7.5-9.0 | 1.0% Water sol, 60° C. pH meter |
| Viscosity | 5.0 mPa · s or more | 1.5%, 75° C., B-type viscometer |

2. Results

From the shell composition in Example 1, a seamless capsule having a diameter of 3 mm was able to be manufactured, with good uniformity of the shell thickness (uneven thickness≈1:1.5) of the capsule, with no eyes (droplets of core material remaining in a shell) confirmed. Also, from the shell composition in Example 2, seamless capsules having a diameter of 3 mm and 4 mm were able to be manufactured, with good uniformity of the shell thickness (uneven thickness≈1:1.5 and 1:1.6), with no eyes confirmed. From the shell composition in Example 3, a seamless capsule having a diameter of 3 mm was able to be manufactured with uniformity of the shell thickness (uneven thickness≈1:2.0) inferior to those in Examples 1 and 2, with some eyes confirmed, though having practicality as a capsule. From the shell composition in Example 4, a seamless capsule having a diameter of about 4 mm was able to be manufactured.

The results described above show that use of the shell composition comprising the present PVA copolymer, agar and the like allows high-quality seamless capsules with good uniformity of the shell thickness, with virtually no (or none at all of) eyes, to be manufactured.

Although hydrophilic polysaccharides other than agar and the like were used to examine combination with a PVA copolymer in the same manner, no capsule was able to be manufactured. Specific examples of hydrophilic polysaccharides other than agar and the like include locust bean gum, xanthan gum, Gelmate (registered trademark) SA (manufactured by DSP Gokyo Food & Chemical Co., Ltd.), Gelmate (registered trademark) KS (manufactured by DSP Gokyo Food & Chemical Co., Ltd.), Gryloid (registered trademark) 2A (tamarind gum, manufactured by DSP Gokyo Food & Chemical Co., Ltd.), guar gum, pectin and gum arabic. In the present invention, the coexistence of the "hydrophilic polysaccharides other than agar and the like" and "agar and the like" may be possible.

Example 5

From the inner cylinder of a concentric double nozzle of a seamless capsule manufacturing apparatus (SPHEREX [inner diameter of discharge aperture of inner nozzle: 0.5 mm, inner diameter of discharge aperture of outer nozzle: 1 mm, inner diameter of upper end opening of formed tube: 22 mm, vibration frequency: 25 Hz, tank temperature: 60° C., set temperature of cooling oil: 5° C.] manufactured by Freund Sangyo Co., Ltd.), a content of 100 parts by mass of Millitol 318 (caprylic/capric triglyceride, manufactured by BASF) and 5 parts by mass of ethanol as core material was discharged to drop at a discharge rate of 2.02 mL/min, and from the outer cylinder, the same shell composition as in Example 1 as shell composition was discharged to drop at a discharge rate of 5.26 mL/min, respectively, into a carrier liquid (medium chain fatty acid triglyceride (MCT), liquid temperature: 5° C.) set at a flow rate of 20000 mL/min into the internal part of the formed tube. The resulting undried capsule was immersed in an MCT liquid (liquid temperature: 4° C.) for 5 days. The capsule in the MCT liquid was collected and left standing at room temperature (20° C.) for 15 hours to be dried, so that a capsule having a shell ratio of 20% was obtained.

The resulting soft capsule was analyzed using a particle image analyzer (device name: Morphologi G3, manufactured by Malvern). As a result, it was found that the capsule had an average particle size of about 700 μm.

Further, the resulting capsule was observed with a high-resolution 3D X-ray microscope (nano3DX-J, manufactured by Rigaku Corporation) and a photochemical microscope (VHX-D510, manufactured by Keyence Corporation). As a result, it was found that the capsule was a nearly spherical soft capsule.

INDUSTRIAL APPLICABILITY

The seamless capsule manufactured using the present shell composition has high quality, with excellent uniformity of the shell thickness of the capsule and virtually no eyes in the shell, being useful in the fields of foods, pharmaceuticals, and cosmetics.

The invention claimed is:
1. A method of manufacturing a seamless capsule, comprising the step of performing a submerged dropping method using a multiple nozzle for a shell composition and a capsule fill, the shell composition comprising agar and a polyvinyl alcohol copolymer, wherein the polyvinyl alcohol copolymer comprises the following as structural units:
(i) polyvinyl alcohol,
(ii) at least one unsaturated carboxylic acid selected from the group consisting of acrylic acid, methacrylic acid, fumaric acid and maleic acid, and
(iii) at least one unsaturated carboxylic acid ester selected from the group consisting of compounds represented by formula [I]:

$$H_2C=C(R^1)-COOR^2 \quad [I]$$

(wherein $R^1$ represents a hydrogen atom or a methyl group, and $R^2$ represents an alkyl group having 1 to 4 carbon atoms).

2. The method of manufacturing a seamless capsule according to claim 1, wherein the unsaturated carboxylic acid is acrylic acid.

3. The method of manufacturing a seamless capsule according to claim 1, wherein the unsaturated carboxylic acid ester is methyl methacrylate.

4. The method of manufacturing a seamless capsule according to claim 1, wherein the shell composition further comprises one or more plasticizers.

5. The method of manufacturing a seamless capsule according to claim 4, wherein the one or more plasticizers are plasticizers comprising glycerol and sorbitol.

6. The method of manufacturing a seamless capsule according to claim 2, wherein the unsaturated carboxylic acid ester is methyl methacrylate.

7. The method of manufacturing a seamless capsule according to claim 2, wherein the shell composition further comprises one or more plasticizers.

* * * * *